United States Patent [19]

Milder et al.

[11] Patent Number: 5,116,305
[45] Date of Patent: May 26, 1992

[54] CURVED INTRA AORTIC BALLOON WITH NON-FOLDING INFLATED BALLOON MEMBRANE

[75] Inventors: Fredric L. Milder, Brookline; Meir Rosenberg, Salem, both of Mass.

[73] Assignee: Abiomed, Inc., Danvers, Mass.

[21] Appl. No.: 780,393

[22] Filed: Oct. 23, 1991

Related U.S. Application Data

[63] Continuation of Ser. No. 474,529, Feb. 1, 1990, abandoned.

[51] Int. Cl.$^5$ .............................................. A61N 1/362
[52] U.S. Cl. ...................................... 600/18; 604/96; 606/192
[58] Field of Search ................................. 600/16–18; 606/191–200; 604/96, 103

[56] References Cited

U.S. PATENT DOCUMENTS

| | | | |
|---|---|---|---|
| 3,939,820 | 2/1976 | Grayzel | 600/18 |
| 4,467,790 | 8/1984 | Schiff | 600/18 |
| 4,527,549 | 7/1985 | Gabbay | . |
| 4,644,936 | 2/1987 | Schiff | 600/18 |
| 4,741,328 | 5/1988 | Gabbay | . |

FOREIGN PATENT DOCUMENTS

244694 4/1989 German Democratic Rep. .
1186216 10/1985 U.S.S.R. .

OTHER PUBLICATIONS

Evans et al. "Development of An Intra-aortic Balloon Assist Device", Artificial Heart Program Proceedings, Jun. 9–13, 1969, Washington, D.C.
Abstract Entitled "Effectiveness of A Counter Pulsation Device Implanted on the Ascending Aorta vs. Intra-Aortic Balloon Pump in Sever Cardiogenic Shock".
Chyong et al. "Aortic Root Balloon Pumping (A.R.B.P.)"—Tokyo Women's College Heart Institute, Department of Surgery, Received for Publication Jan. 5, 1971.
Moulopoulos, "Systolic Counterpulsation with a Small Balloon to Increase Coronary Flow".
Brown et al.—"Improved Intraaortic Balloon Diastolic Augmentation with a Double-Balloon Catheter in the Ascending and the Descending Thoracic Aorta".
Department of Biomedical Engineering, The Johns Hopkins University School of Medicine, vol. 6 No. 2—Aug. 1968.

Primary Examiner—Lee S. Cohen
Assistant Examiner—J. P. Lacyk
Attorney, Agent, or Firm—Lahive & Cockfield

[57] ABSTRACT

An intra aortic balloon pumping device comprises a pumping balloon, an attached inflation catheter, a supporting member which is disposed within and extends from the catheter into the balloon. The balloon membrane of the invention resists the formation of membrane folds in the tail section of the balloon. This characteristic of the balloon membrane is believed to result from the addition of tension to the balloon membrane. Tension may be applied to the membrane by ensuring that the portion of the support member which is disposed within the balloon is equal to the length of the outer curve of the balloon wall such that it resides on an outer curve of the wall. Alternatively, tension may be applied by extending the support member within the balloon.

24 Claims, 6 Drawing Sheets

CURVED INTRA AORTIC BALLOON WITH NON-FOLDING INFLATED BALLOON MEMBRANE

This is a continuation of copending application Ser. No. 07/474,529 filed on Feb. 1, 1990 now abandoned.

BACKGROUND OF THE INVENTION

The present invention relates to devices such as intra aortic balloon pumps (IABPs) wherein an inflatable envelope or balloon mounted on the end of a long catheter is inserted through a blood vessel to a position in the aorta where it is operated to supplement the cardiac pumping action.

The use of catheter supported balloons as devices to assist blood circulation from an ailing heart is now a well recognized medical technique. In a typical prior art construction, a manifold or handle is mounted to provide a separate fluid connection to each of an inner and an outer tube, which extend for a length of one-half to one meter from the handle. At the far ends of the tubes a balloon is mounted to be inflated by the outer tube, while the inner tube extends through the balloon to provide a lumen for sampling or administering fluids on the far (cardiac) side of the balloon. Various balloon shapes are known.

Insertion of the balloon to a site in the aorta is accomplished by first compacting the uninflated balloon, by folding, wrapping, twisting or the like, and then inserting the compacted balloon assembly through an artery using a guide wire and/or sheath to guide it past irregularities or branches in the artery. Care must be taken during insertion to avoid trauma or perforation, particularly when the balloon is passing branches or curves of the artery.

Balloons have also been designed with a curved shape to better enable the balloon to follow a curved arterial passage or to permit the balloon to remain stably positioned in a curved arterial section during pumping. An example of such a balloon is described in U.S. patent application Ser. No. 257,752 filed Oct. 14, 1988.

When intra aortic balloons (IAB) as described in application Ser. No. 257,752 are inflated within the aorta, a pressure differential along the length of the balloon develops. As a result, the cardiac (forward) end of the balloon is exposed to a higher pressure than the opposite (tail) end of the balloon. This pressure differential may cause an undesirable folding in the tail end of the balloon. The folding of the balloon reduces the lifetime and reliability of the device as it adds stress to the balloon membrane and could eventually lead to premature failure. It would be advantageous to provide an IAB which would exhibit a relatively long operational life.

It is thus an object of the invention to provide a reliable insertable arterial balloon assembly adapted to be positioned in a curved arterial passage. It is another object of the invention to provide an insertable arterial balloon assembly having a curved balloon support structure which is better able to resist the formation of fabric folds at its tail end during intra aortic balloon pumping. A further object of the invention is to provide a balloon reliable in actual use, which may also be easily compacted and prepared for insertion into the body. Other objects will be apparent to those skilled in the art upon reading the following disclosure.

SUMMARY OF THE INVENTION

Broadly, the invention provides a curved intra aortic balloon, the membrane of which is maintained under slight tension in the inflated condition. The tensioning of the balloon membrane has been found to prevent, or significantly minimize, the tendency of the balloon to form folds in its tail end (i.e., the end exposed to lower pressure and typically distal to the heart) while in the inflated condition.

The balloon, constructed of a polymeric membrane, has a longitudinal axis which may be straight, but preferably is slightly curvilinear. In the inflated condition the maximum diameter of the balloon along the short axis lies in a plane transverse to the long axis of the balloon and is positioned intermediate the ends of the balloon. Preferably, the diameter of the balloon tapers from the area of greatest diameter toward each end of the balloon with the plane of maximum diameter closer to the tail end than to the front end.

A catheter for supplying a fluid or gas to control the inflation of the balloon is attached to the end distal to the heart (tail end) of the balloon. At this tail end the balloon tapers to approximately the diameter of the catheter. A member, which serves to provide support and a curvilinear shape to the inflated balloon, is disposed within and extends from the catheter into the balloon where it terminates at the tip of the balloon which is proximal to the heart. Preferably this member is a second, or interior, pressure monitoring lumen (PML) which also provides a pressure and/or fluid monitoring function, as well as a fluid administration function. In a preferred embodiment, the PML is adjacent to and in contact with the outer curve of the balloon membrane while the balloon is inflated. The second lumen preferably is equal in length to the outer curve of the balloon wall. It has been found that by making the member of a length which is at least equal to that of the outer curve of the balloon wall, tension is imparted to the entire balloon membrane. This tension prevents, or substantially minimizes, the tendency of the inflated balloon to form folds during pumping. Most preferably, the portion of the outer wall upon which the second lumen resides is of a thickness slightly greater than the remainder of the balloon membrane.

In another embodiment of the invention, the portion of the second lumen disposed within the balloon need not initially be of a length equal to that of the outer curve of the balloon wall. Instead, tension may be imparted to the membrane of the inflated balloon by extending the second lumen forward toward the cardiac end of the balloon. The forward displacement of the second lumen applies tension to the balloon membrane to eliminate the presence of excess membrane in the tail end which would lead to the formation tail folds.

The invention also provides a method of folding the balloon in which a compact structure, easily inserted into an artery, is formed.

DETAILED DESCRIPTION OF THE INVENTION

Intra aortic balloon pumps "IABPs" and their method of operation are now well known in the art. The balloon component of IABPs may be substantially linear or may be curved. Curved balloon structures are disclosed in U.S. patent application Ser. Nos. 257,752 filed Oct. 14, 1988 and 259,056 filed Oct. 18, 1988, both of which are hereby incorporated by reference.

With compliant balloons of the type particularly applicable to the present invention, the balloon dimensions change as a function of transmembrane pressure. The balloon is designed to operate under positive transmembrane pressure, which is partially a function of the diameter of a vessel which it is to occlude. Generally, the higher the transmembrane pressure, the greater the balloon diameter and volume should be. As long as positive transmembrane pressure exists, there is less likelihood of folding of the balloon membrane. Often balloon folding can be eliminated by controlling the internal pressure and diameter of the balloon.

Figure 1:
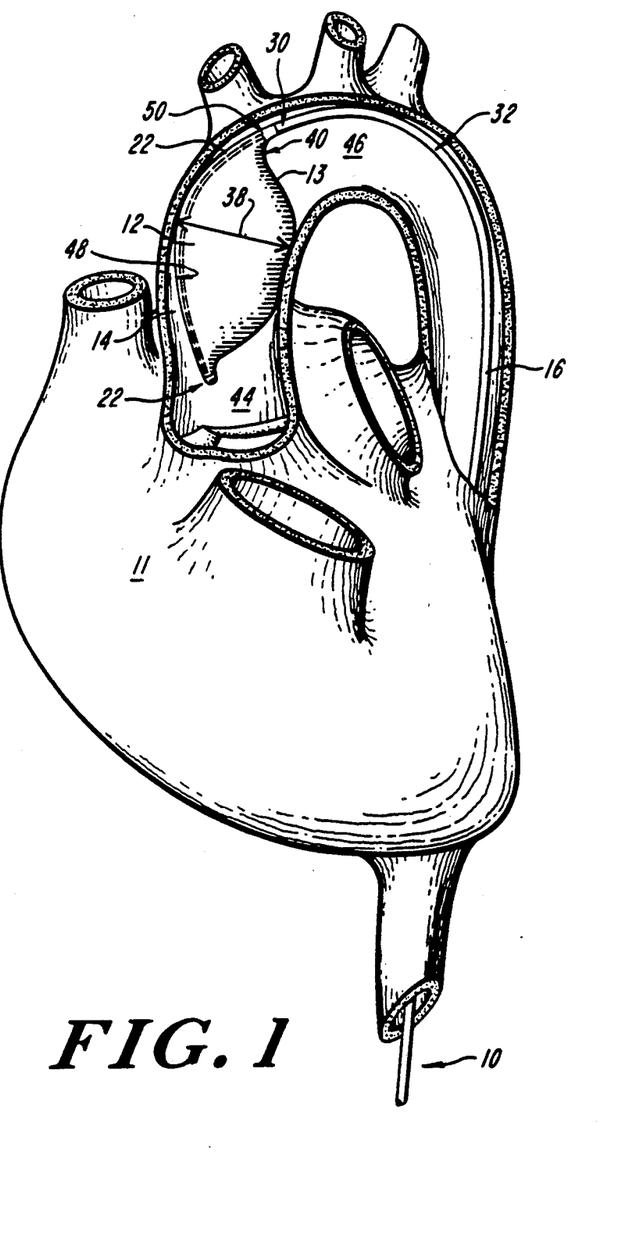
FIG. 1 is a perspective view of an inflated catheter balloon of the invention positioned within the ascending aorta.

FIG. 1 generally illustrates the application of an intra aortic balloon (IAB) device 10 of the present invention in which a catheter balloon 12 having an inflatable balloon membrane is positioned in an inflated condition within the ascending aorta 14.

Figures 2, 3:
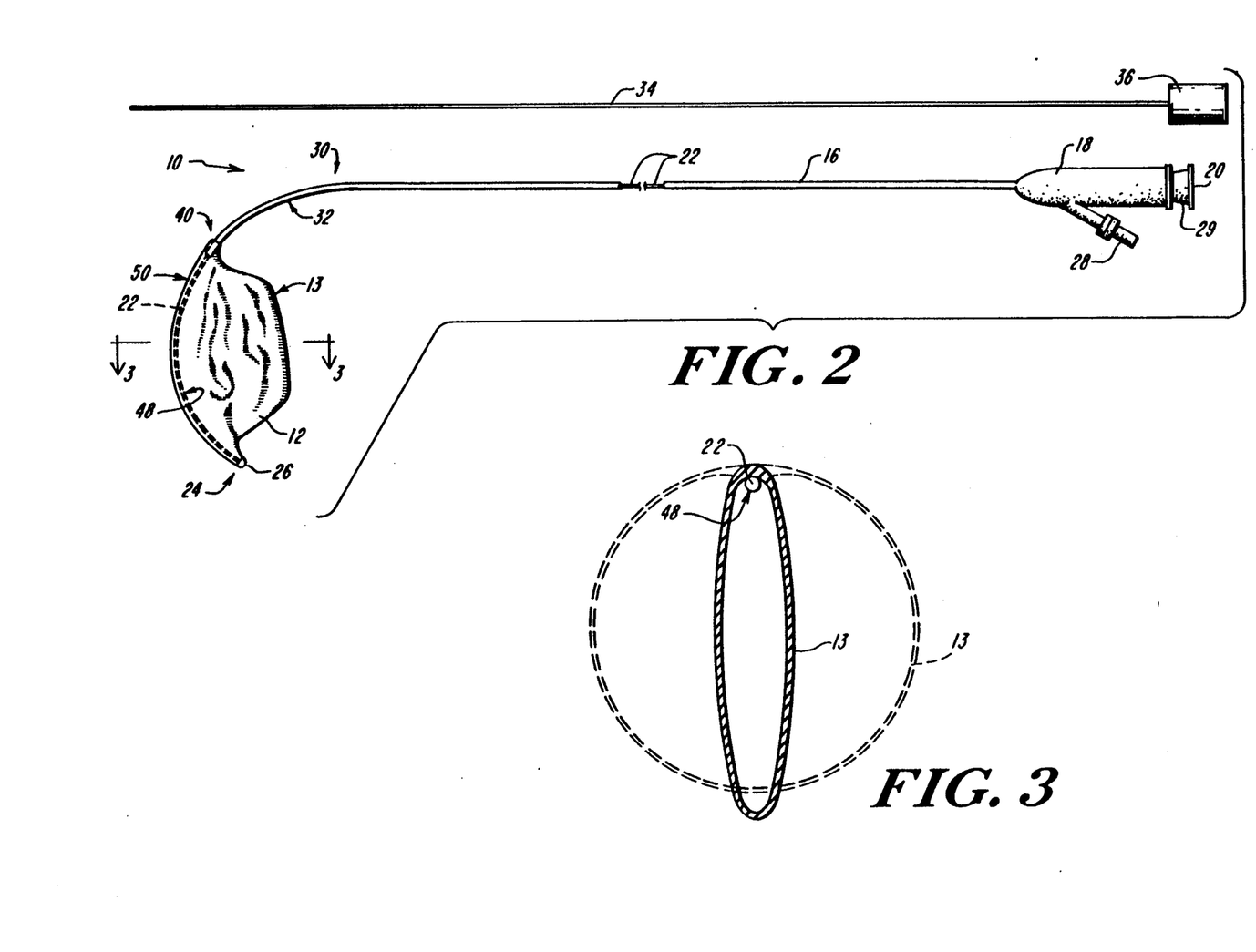
FIG. 2 is a generally plan view of an intra aortic balloon device according to the present invention with the balloon in the deflated position.
FIG. 3 is a sectional view along lines 3—3 of the balloon illustrated in FIG. 2.

Referring to FIGS. 1 and 2, the IAB device of the present invention comprises an inflation catheter 16 connected between a catheter balloon 12 on one end and a handle 18 on the other end. The handle 18 serves as a fluid manifold for connection to a pulsed source of inflation fluid via port 28. The catheter 16 has disposed therein a member (or inner lumen) 22 which extends from handle 18 to the tip 24 of the balloon which is proximal to the heart. The inner lumen 22 preferably is a hollow pressure monitoring lumen (PML) which connects a pressure monitoring and fluid sampling port 26 at the proximal end 24 of the balloon 12 with a second port 20 on handle 18. As such, member 22 serves to monitor pressure and fluids on the cardiac side of the balloon as well as to provide support and curvature to the balloon. Alternatively, lumen 22 may simply be a support member constructed of a hollow or solid material.

Figure 6A:
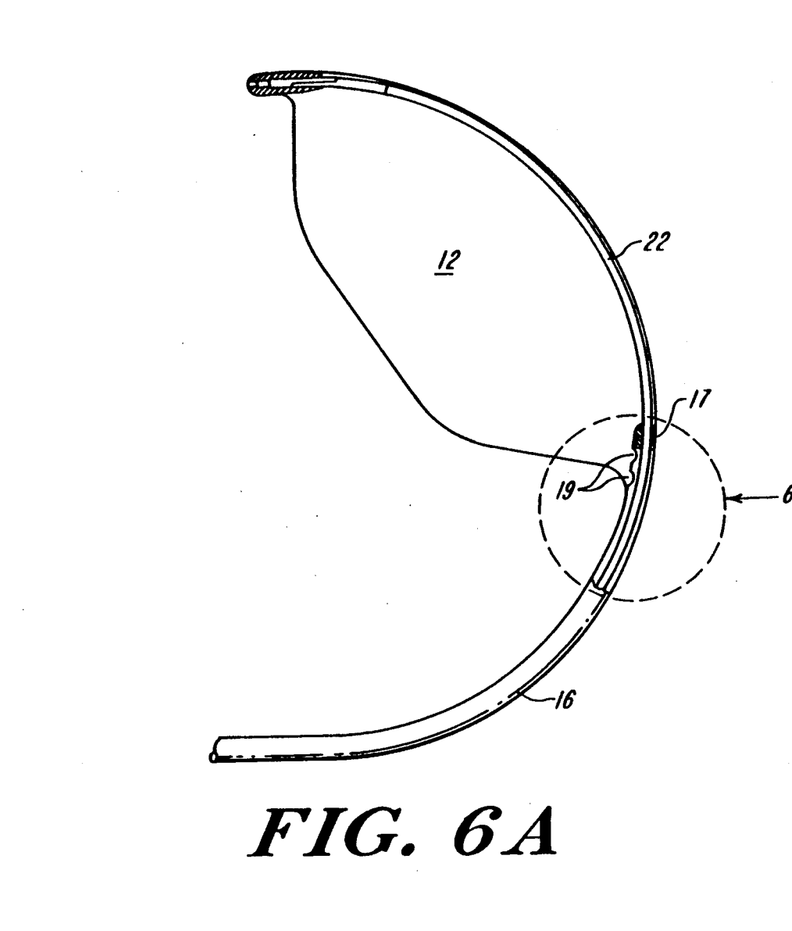
FIG. 6A is a sectional view of an intra aortic balloon of the present invention.
Figure 6B:
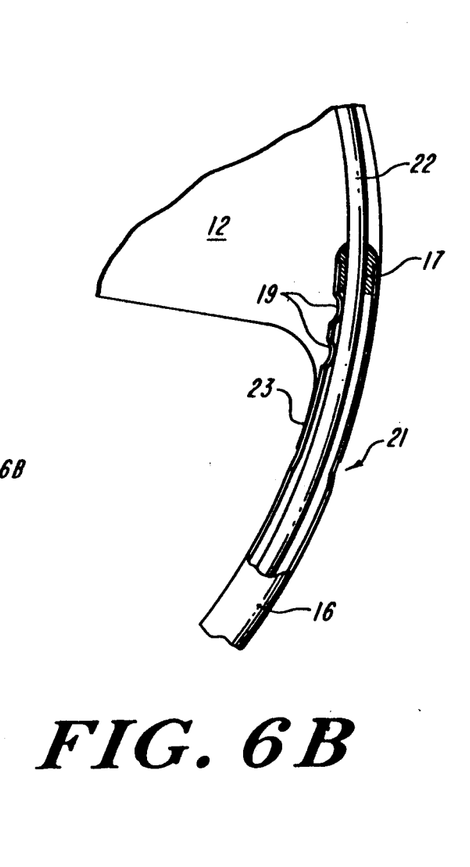
FIG. 6B is a detail view of a portion of FIG. 6A.

The inflation catheter 16 and lumen 22 may be constructed and joined in virtually any manner known in the art. FIGS. 6A and 6B, however, illustrate a preferred embodiment in which a bushing 17 is disposed at an end of inflation catheter 16, forward of vents 19. The bushing 17 fits securely within the terminal end of catheter 16 and surrounds lumen 22. This construction is advantageous as bushing 17 prevents relative movement, such as rotational movement, between inflation catheter 16 and lumen 22. As also illustrated in FIG. 6B, the diameter of catheter 16 may be reduced toward a terminal portion of the catheter, preferably at approximately location 21 where the end of the balloon 23 envelopes catheter 16.

Figure 7A:
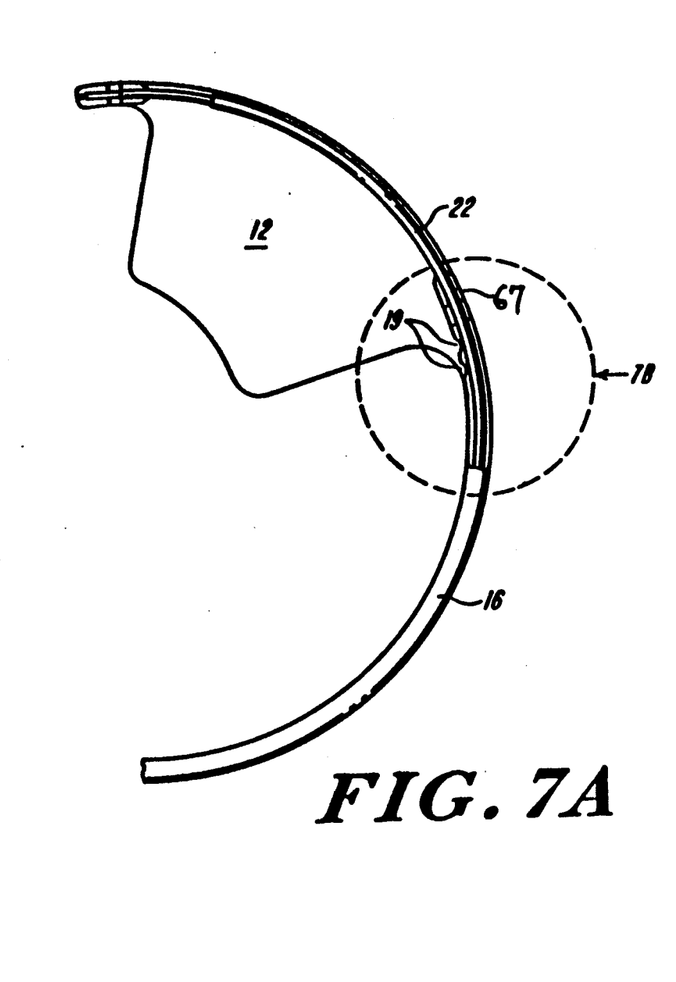
FIG. 7A is a sectional view of an intra aortic balloon of the present invention.
Figure 7B:
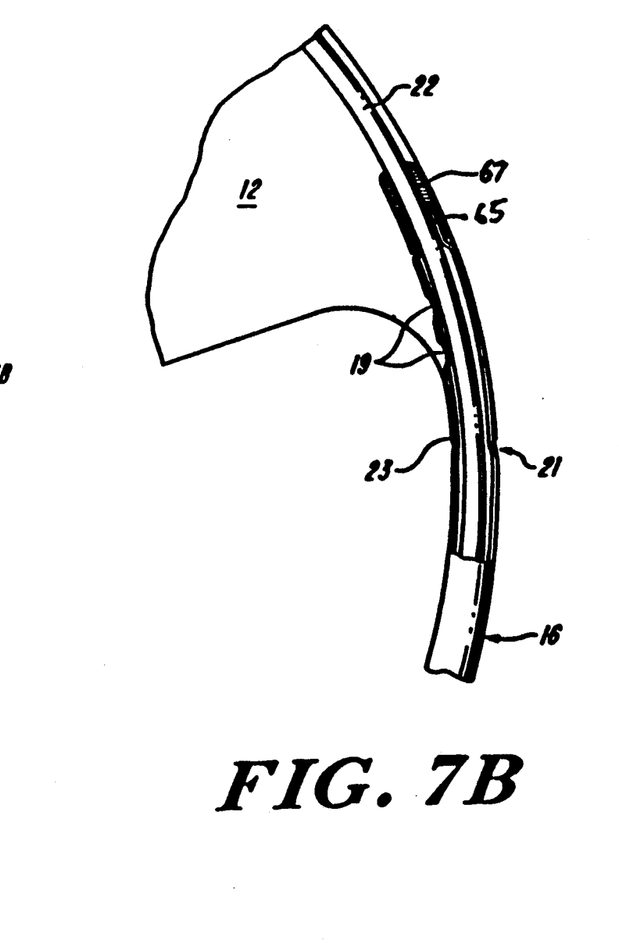
FIG. 7B is a detail view of a portion of FIG. 7A.

Alternatively, relative rotational movement of the catheter 16 and lumen 22 may be prevented in the manner illustrated in FIGS. 7A and 7B. As illustrated, the terminal end 65 of catheter 16 decreases in diameter until its inside diameter is substantially equal to the outside diameter of lumen 22. The tapered end 65 of catheter 16 may have a cap element 67 inserted thereon. The cap element 67 preferably is made of a radiopaque material such as steel.

In a currently preferred embodiment, the balloon end 30 of the IAB device 10 is cylindroidal in shape and is formed with an intrinsic curvature such that both the balloon 12 and the adjacent terminal portion 32 of inflation catheter 16 are curved. A separate stiffening member 34, illustrated in FIG. 2 as removed from the device, is adapted to fit within the inflation catheter 16 and lumen 22 for straightening the curved end of the device 10 during the initial stages of balloon insertion. The stiffening member 34 fits within a central port, e.g., port 20, and may be extended through the inner lumen 22 and/or inflation catheter 16 to the balloon tip 24. When the stiffening member 34 is inserted it overcomes the intrinsic curvature of the balloon end 30 of the device 10. Knob 36, mounted to the end of member 34, locks to a mating fitting on handle 18 by a bayonet mount, locking Luer fitting, or the like, 29 to secure the member in position.

As noted above, the balloon 12 is cylindroidal, having a curved, generally elongate structure. In the inflated condition, shown in FIG. 1, the balloon has maximum diameter transverse to its longitudinal axis at a plane 38, somewhat behind the midpoint of the balloon along the balloon's longitudinal axis. From its end 24 proximal to the heart, the inflated balloon increases in diameter to its maximum diameter 38. The diameter of the balloon then decreases from point 38 to the distal end 40 of the balloon. The balloon at distal end 40 tapers such that the end of inflating catheter 16 fits within and is secured to the balloon. When the balloon is inflated, its largest diameter is sufficient to occlude the aorta. The wall thickness of the balloon membrane 13 typically is approximately 3-5 mils, however, the membrane may feature reinforced areas of increased thickness which may be from about 1.2 to 1.6 times thicker than the remainder of the wall.

As previously mentioned "tail folding" is a phenomenon which results in the occurrence of indentations in which portions of the balloon membrane in the distal (tail) end 40 of the balloon 12 buckle and extend into the balloon interior. Tail folding tends to weaken the balloon and may result in membrane failure after extended use. It is believed that this phenomenon is due to a combination of the shape of the balloon membrane coupled with the pressure gradient between the proximal 24 and distal 40 ends of the balloon. According to the invention, tail folding is eliminated, or greatly reduced, by placing the entire balloon membrane under tension.

In one embodiment, illustrated in FIGS. 1 through 3, the inner lumen 22 preferably has a terminal section 48 disposed within balloon 12. Terminal section 48 is substantially equal in length to the outer curve 50 of the balloon wall. The equal lengths of the balloon wall and terminal section 48 of lumen 22 results in the application of tension to the balloon membrane. Also, the terminal section 48 deforms to fit within the balloon and to match the curvature of the balloon, thus causing it to contact the outer curve 50 of the balloon wall throughout its length. The tension applied to the balloon membrane eliminates the availability of excess material in the tail end of the balloon which otherwise may form tail folds. In a preferred embodiment the membrane wall at outer curve 50 has a thickness slightly greater than the thickness of the remaining portions of the wall. Preferably, the thickness of wall at the outer curve 50 is 1.2 to 1.6 times greater than the wall thickness of the remaining areas of the balloon membrane. The balloon length, from tip to tail, preferably is approximately 100 mm.

Figure 4:
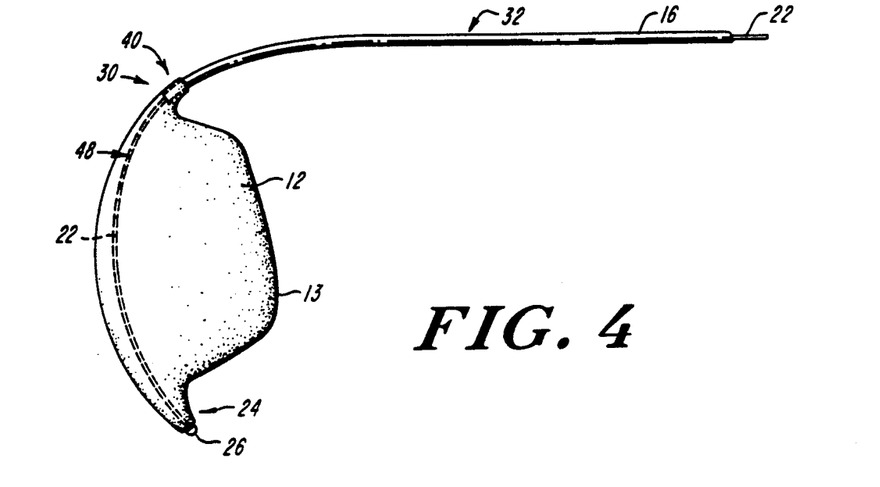
FIG. 4 is a perspective view of a deflated intra aortic balloon pump according to another embodiment of the invention in which a member disposed within the balloon is laterally displaceable.

In another embodiment, illustrated in FIG. 4, tension may be applied selectively to the balloon membrane by advancing the lumen 22 so as to increase the effective length of the terminal section 48 of lumen 22 which is disposed within balloon 12. In doing so, the lumen 22 will press against the proximal tip 24 of the balloon, causing the balloon membrane to be stretched and thus eliminate the availability of the excess membrane which could form tail folds. Sufficient tension may be applied to the balloon membrane to eliminate tail folding by extending the lumen 22 within the balloon by an amount sufficient to bring the lumen 22 into contact with the interior wall 51 of the balloon.

As noted earlier, lumen 22 preferably is a hollow lumen used to monitor pressure and to sample fluids on the cardiac side of the balloon. Alternatively, lumen 22 may be a solid or hollow member which simply provides support and assists in maintaining balloon curvature. In either case, lumen 22 may be manufactured of a polymeric material, such as polyurethane, by known extrusion techniques. Exemplary polyurethane materials from which lumen 22 may be manufactured include those sold by Dow Chemical Company under the trade name "Isoplast 101". In other embodiments member 22 may consist of a spiral wound wire tube or the like. Catheter 16, like lumen (or member) 22, may also be formed of similar polyurethane materials, using known extrusion techniques.

The balloon typically is manufactured by dip coating a mandrel with a polymeric material such as polyurethane. Preferred polyurethanes include "Texin", available from Mobay Chemical company; "Avcothene - 51", available from Kontron Cardiovascular, Inc. "Angioflex" available from Abiomed, Inc., and "Biomer" available from Ethicon, Inc. In a preferred embodiment the volumetric compliance of the balloon membrane is about 5 to 15 cc/100 mm Hg transmembrane pressure. The preferred diameter compliance of the balloon membrane ranges from about 2–5 mm/100 mm Hg transmembrane pressure. These compliance values are based upon a balloon having a nominal volume of 45 cc. Compliance values are expected to change relative to changes in the nominal volume of the balloon.

In many manufacturing techniques, the balloon is formed in an inflated shape in a three dimensional condition on a mandrel. However, in a preferred embodiment the balloon is formed upon a thin, flat die so that it is manufactured in a substantially two-dimensional condition.

Following the extrusion of catheter 16, it is heat-formed to produce at its terminal end a radius of curvature of about 2 to 5 centimeters in a region of tubing extending over a distance of about 10 to 20 centimeters from the end of the catheter. Lumen 22 similarly is subjected to a heat-forming process to attain a similar degree of curvature. Virtually any technique may be utilized to attain similar degrees of curvature for catheter 16 and lumen 22. For example, the lumen 22 may be placed inside, or along side, the catheter 16, and the two tubes may then be aligned in a jig such that the curvature of lumen 22 matches that of the terminal end of catheter 16. With the tubes held in this alignment, the balloon and handle may then be mounted at opposed ends of the assembly. Suitable assembly techniques for attaching the balloon are well known and include solvent bonding, RF welding, heat welding and adhesive or other bonding. During assembly, radio opaque markers are placed at the end of the catheter and at the end of lumen 22, in a manner known in the art. This permits fluoroscopic visualization of the balloon and its direction of curvature during insertion.

Stiffening member 34 may be constructed of nineteen gauge regular wall stainless steel tube stock. This material provides adequate stiffness and resistance to lateral bending so that member 34 may overcome the curvature of the inflation catheter and lumen 22. While a solid metal rod, preferably a wire under one millimeter in diameter, could also be used, the steel tubing is preferred because it may be placed over a guide wire to facilitate insertion of the balloon assembly in a blood vessel.

Figure 5A:
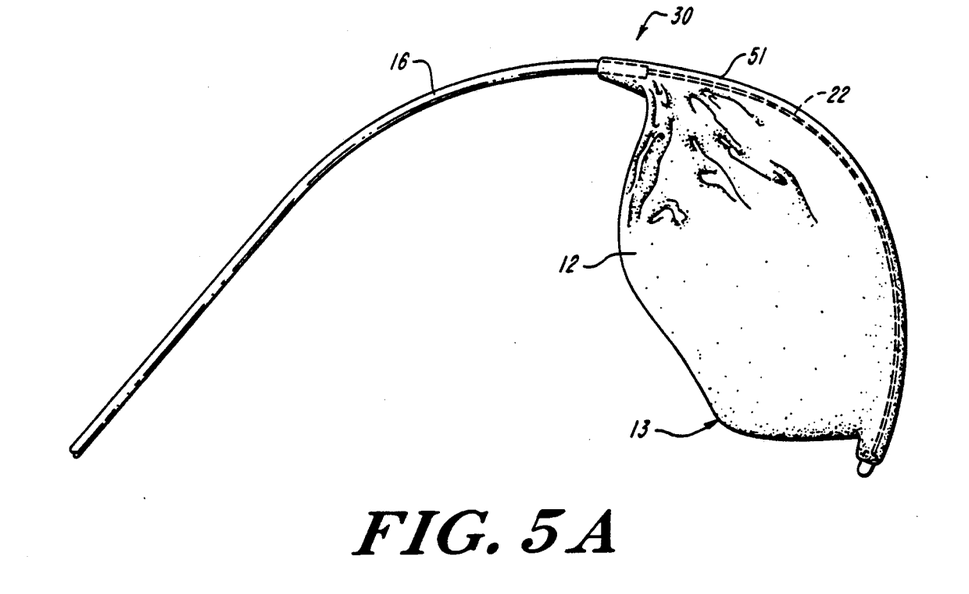
FIGS. 5A through 5E are schematic views illustrating the method of folding a balloon according to the present invention.
Figure 5B:
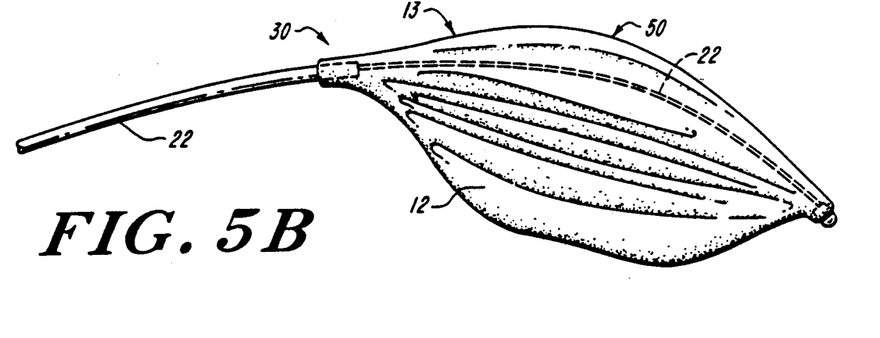
Figure 5C:
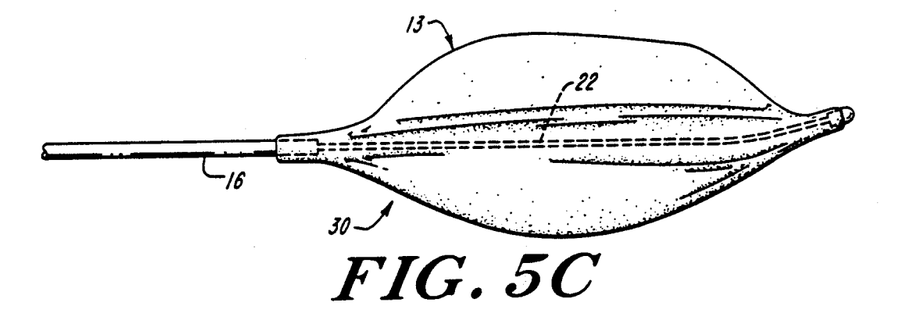
Figure 5D:
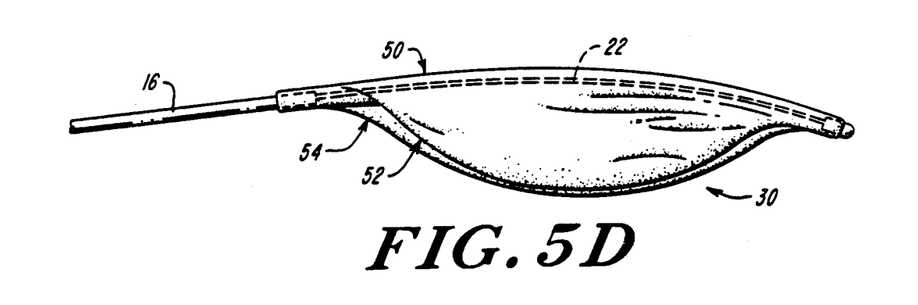
Figure 5E:
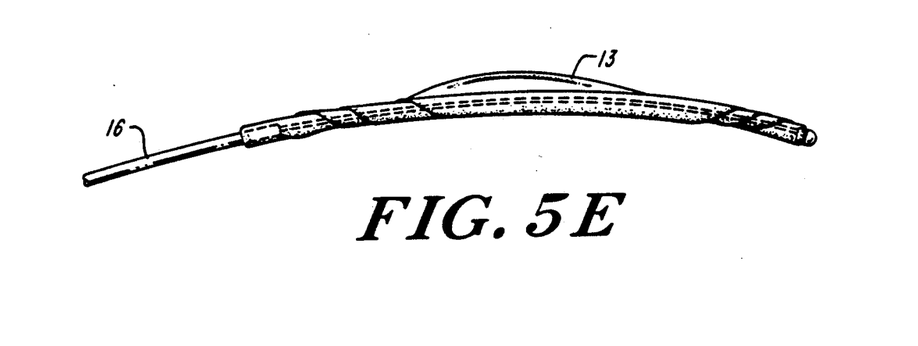

FIGS. 5A through 5E illustrate another aspect of the invention which permits more compact wrapping of the balloon 12 and facilitates ease of insertion of the balloon 12 into an artery. In FIG. 5A the balloon 12 and the terminal end of the catheter 32 assume a curved profile, and lumen 22 resides on the outer curve 50 of the balloon membrane as in the embodiment illustrated in FIGS. 1 through 3. The balloon 12 illustrated in FIG. 5A is in the deflated condition and the balloon membrane hangs down from and is supported by lumen 22. The balloon of FIG. 5A is prepared for wrapping and insertion by first inserting a stiffening member 34 through the lumen 22 such that it extends to the tip 24 of the balloon. As shown in FIG. 5B, this step results in a straightening (and stretching) of the terminal end 32 of the inflation catheter 16 and of the balloon 12. At the same time, lumen 22 is drawn away from the outer curve 50 of the balloon membrane 13. Next, as illustrated in FIG. 5C, the lumen 22 is manually moved to the center of the balloon and the balloon is fully evacuated, causing lumen 22 to be pressed between the two opposed walls of the membrane 13 and thus held in place. As further illustrated in FIG. 5D, the balloon membrane 13 is completely flat and the lumen 22 is positioned at a central portion of the balloon 12. In this configuration the balloon has left 52 and right 54 segments which fold over lumen 22. The balloon may be wrapped around the lumen 22 by wrapping both the left 52 and right 54 segments of the balloon 12 around the lumen 22 in the same direction in a generally spiral configuration as illustrated in FIG. 5E. This procedure yields a compact, easily insertable IABP device.

Although it is preferable to insert the stiffening member 34 through lumen 22 while wrapping the balloon, it is also possible to wrap a balloon by inserting a stiffening member into the interior of the balloon, alongside lumen 22. Also, it is possible to utilize a stiffening member having a diameter greater than that of the lumen and to insert the stiffening member such that it surrounds all or part of the lumen.

Although particular embodiments of this invention have been described and are illustrated herein, it is recognized that modifications and variations may readily occur to those skilled in the art. For example, the invention comprehends other forms of insertable balloon apparatuses, with differing balloons, intrinsic curvatures, number of lumens, and having curved or uncurved lengths of adjacent catheter. Consequently, it is intended that the claim be interpreted to cover such modifications and equivalents.

What is claimed is:

1. A cardiac assist device for insertion into the aorta, comprising:
    a pumping balloon having a membrane formed in a generally cylindroidal inflated shape wherein the maximum diameter in a plane transverse to the long axis of the balloon is located intermediate the ends of the balloon and wherein the balloon diameter decreases in both directions from the plane of largest diameter along said axis;
    a catheter means for providing fluid to the balloon when the balloon is positioned within the aorta, said catheter means being joined at a terminal end thereof to one end of the balloon; and
    a support member tensioning the inflated balloon membrane, said support member being located within and extending the length of the balloon, the support member also being in contact with an interior surface of the balloon membrane, said balloon membrane being stretched along the length of its surface contacting said support member to provide said tensioning.

2. The device of claim 1 wherein the support member is disposed within and extends from the terminal end of the catheter means.

3. The device of claim 2 wherein a bushing is mounted within the catheter means and surrounds the support member to prevent relative rotational movement of the catheter means and the support member.

4. The device of claim 2 wherein the diameter of said catheter means decreases, at the terminal end to engage outer walls of said support member to prevent relative rotational movement of the catheter means and the support means.

5. The device of claim 1 wherein the inflated balloon and the support member are curved, such that said balloon has an inner curved wall and a longer, outer curved wall and wherein said support member is in contact along substantially the entire length of the interior surface of the outer curved wall and has a length substantially equal to that of the outer curved wall.

6. The device of claim 5 wherein the inflated balloon and the support member have a curved portion with a characteristic radius of curvature in the range of approximately 2 to 5 centimeters.

7. The device of claim 5 wherein the inflated balloon and the support member have a curved portion which approximately conforms to the curvature of the aortic arch.

8. The device of claim 5 wherein the outer curve of the balloon membrane wall is thicker than the remainder of the balloon membrane wall.

9. The device of claim 8 wherein the ratio of the thickness of the outer curve of the balloon membrane to the of the remainder of the balloon membrane wall is in the range of about 1.2:1 to 1.6:1.

10. The device of claim 5 wherein said terminal end of the catheter means has a curvature substantially equal to that of the support member.

11. The device of claim 1 wherein said balloon is formed in a substantially flat condition.

12. The device of claim 1 wherein said support member is a hollow tube.

13. The device of claim 12 wherein said hollow tube is a pressure monitoring lumen.

14. The device of claim 1 wherein said support member is a solid member.

15. The device of claim 1 wherein the balloon is formed of a thin elastomeric material, said balloon having a volumetric compliance within the range of about 5 to 15 cc/100 mm Hg transmembrane pressure.

16. The device of claim 13 wherein the compliance is approximately 7 cc/100 mm Hg transmembrane pressure.

17. The device of claim 1 wherein the balloon is formed of a thin elastomeric material, said balloon having a diameter compliance in the range of about 2-5 mm/100 mmHg transmembrane pressure.

18. A cardiac assist device for insertion into the aorta, comprising:
    a pumping balloon having a membrane formed in a generally cylindrical inflated shape wherein the maximum diameter in a plane transverse to the long axis of the balloon is located intermediate the ends of the balloon and wherein the balloon diameter decreases in both directions from the plane of maximum diameter along said axis;
    a catheter means for providing fluid to the balloon when the balloon is positioned within the aorta, said catheter means being joined at a terminal end thereof to one end of the balloon; and
    an extensible support means for selectively tensioning the balloon membrane, said support means located within said balloon and upon extension extending the length of the balloon to impart tension to said membrane.

19. A method of wrapping a balloon of an intra aortic balloon pumping device, comprising the steps of:
    providing an intrinsically curved IAB device having a deflated balloon having a membrane including an inner curved wall and an outer curved wall with a hollow support member extending therethrough, said support member residing against an interior surface of said outer curved wall of the balloon membrane and imparting tension to the balloon membrane;
    inserting a straightening member through the interior volume of the balloon to reduce the intrinsic curvature of the device;
    removing the support member from contact with the outer curve of the balloon member;
    evacuating the balloon to render the balloon membrane substantially flat and disposing the support member at a substantially central portion of the balloon membrane with balloon membrane segments on either side of the support member; and
    simultaneously wrapping both membrane segments around the support member in the same direction.

20. The method of claim 19 wherein the insertion step involves inserting a straightening member through the hollow support member.

21. The method of claim 19 wherein the insertion step involves inserting a straightening member which encompasses at least a portion of the hollow support member.

22. A cardiac assist device for insertion into the aorta, comprising:

a pumping balloon having a membrane formed in a generally cylindroidal inflated shape wherein the maximum diameter in a plane transverse to the long axis of the balloon is located intermediate the ends of the balloon and wherein the balloon diameter decreases in both directions from the plane of largest diameter along said axis;

a catheter means for providing fluid to the balloon when the balloon is positioned within the aorta, said catheter means being joined at a terminal end thereof to one end of the balloon;

a support means for tensioning the balloon membrane, said support means located within the balloon; and a bushing means for preventing relative rotational movement of the catheter means and the support means, said bushing means mounted within the catheter means and extending around at least a portion of said support means.

23. A cardiac assist device for insertion into the aorta, comprising:

a pumping balloon having a membrane formed in a generally cylindroidal inflated shape wherein the maximum diameter in a plane transverse to the long axis of the balloon is located intermediate the ends of the balloon and wherein the balloon diameter decreases in both directions from the plane of largest diameter along said axis;

a catheter means for providing fluid to the balloon when the balloon is positioned within the aorta, said catheter means being joined at a terminal end thereof to one end of the balloon; and a support means for tensioning the balloon membrane, said support means located within the balloon;

said catheter means having a diameter at said terminal end which tapers so as to engage said support means such that an inner diameter of the catheter means is substantially equal to an outer diameter of the support means.

24. The device of claim 23 further comprising a radiopaque cap element secured to the tapered diameter of the catheter means.

* * * * *

UNITED STATES PATENT AND TRADEMARK OFFICE
CERTIFICATE OF CORRECTION

PATENT NO. : 5,116,305
DATED : May 26, 1992
INVENTOR(S) : Fredric L. Milder and Meir Rosenberg It is certified that error appears in the above-indentified patent and that said Letters Patent is hereby corrected as shown below:

Claim 9, column 7, lines 62-65, should read
--The device of claim 8 wherein the ratio of the thickness of the outer curve of the balloon membrane to the thickness of the remainder of the balloon membrane wall is in the range of about 1.2:1 to 1.6:1.--

Signed and Sealed this

Twelfth Day of March, 1996

*Attest:*

BRUCE LEHMAN

*Attesting Officer*     Commissioner of Patents and Trademarks